United States Patent [19]
Okada et al.

[11] Patent Number: 5,164,193
[45] Date of Patent: Nov. 17, 1992

[54] SUSTAINED-RELEASE TABLET

[75] Inventors: Minoru Okada, Inzai; Tetsuo Hayashi, Tomisato; Shuichi Kasai, Narita; Akira Iwasa, Yotsukaido, all of Japan

[73] Assignee: SS Pharmaceutical Co., Ltd., Tokyo, Japan

[21] Appl. No.: 732,927

[22] Filed: Jul. 19, 1991

[30] Foreign Application Priority Data

Jul. 25, 1990 [JP] Japan .................................. 2-197019

[51] Int. Cl.⁵ .............................................. A61K 9/22
[52] U.S. Cl. ...................................... 424/468; 424/465
[58] Field of Search .............. 424/487, 464, 468, 490, 424/491

[56] References Cited

U.S. PATENT DOCUMENTS 4,863,744  9/1989  Urquhart et al. ................. 424/484

FOREIGN PATENT DOCUMENTS 213083  3/1987  European Pat. Off. .

*Primary Examiner*—Thurman K. Page
*Assistant Examiner*—James Spear
*Attorney, Agent, or Firm*—Oblon, Spivak, McClelland, Maier & Neustadt

[57] ABSTRACT

A sustained-release tablet is disclosed. The tablet is a combination of powder (A) comprising an oil component, water insoluble polymer, or both, and a pharmaceutically active component and powder (B) comprising a water soluble polymer and a pharmaceutically active component. An ideal release rate for individual pharmaceutically active component can easily be ensured by controlling its release rate by changing the ratio of powders (A) and (B).

18 Claims, 9 Drawing Sheets

SUSTAINED-RELEASE TABLET

BACKGROUND OF THE INVENTION

1. Field of the Invention

The present invention relates to a sustained-release tablet which can exhibit the effect of pharmaceutically active components contained therein without fail by the administration of one or two times a day, because of its capability of controlling the release rate of the pharmaceutical components with excellent reproducibility.

2. Description of the Background Art

Tablets are a preparation form of drugs which is most widely accepted, because they are more easily administered than capsules and granules.

The increasing demands of reducing the burden imposed to patients by decreasing dosing frequencies of drugs and the requirement of decreasing side effects of drugs by controlling their blood concentration have brought about the recent development in the sustained-release techniques of drug preparations. There have been reports on sustained-release tablets, such as coating tablets coated with a release-controlling coat, matrix tablets comprising water soluble polymeric compounds (Japanese Patent Laid-open (kokai) No. 290818/1988), matrix tablets comprising wax (Japanese Patent Laid-open (kokai) No. 59632/1984), matrix tablets comprising water insoluble polymeric compounds (Japanese Patent Laid-open (kokai) No. 21002/1984), and the like.

All these sustained-release tablets have been with difficulty in controlling the release rate of techniques and studies over a long period time were needed obtain tablets with a desired release rate. Furthermore, the need of complicated processes in the preparation of conventional sustained-release tablets made it difficult to obtain a product with a reproducible release rate. The attempts to obtain tablets with a controlled release rate sometimes encountered with problems in quality control.

Therefore, development of sustained-release tablets which exhibit a controlled release rate, can be manufactured with excellent reproducibility, and can easily ensure the effect of pharmaceutically active components without fail by the administration of one or two times a day has been strongly desired.

In view of this situation, the present inventors have undertaken extensive studies on sustained-release tablets, and have found that a combination of (A) a sustained-release powder comprising an oil component and/or a water insoluble polymer and a pharmaceutically active component and (B) a sustained-release powder comprising a water soluble polymer and a pharmaceutically active component could easily ensure a release rate which is controlled according to the purpose, and that tablets with a reproducible release rate could be manufactured.

SUMMARY OF THE INVENTION

Accordingly, an object of the present invention is to provide a sustained-release tablet which comprises, (A) a sustained-release powder comprising at least one member selected from the group consisting of oil components and water insoluble polymers, and a pharmaceutically active component and (B) a sustained-release powder comprising a water soluble polymer and a pharmaceutically active component.

Other objects, features and advantages of the invention will hereinafter become more readily apparent from the following description.

DETAILED DESCRIPTION OF THE INVENTION

Figure 1:
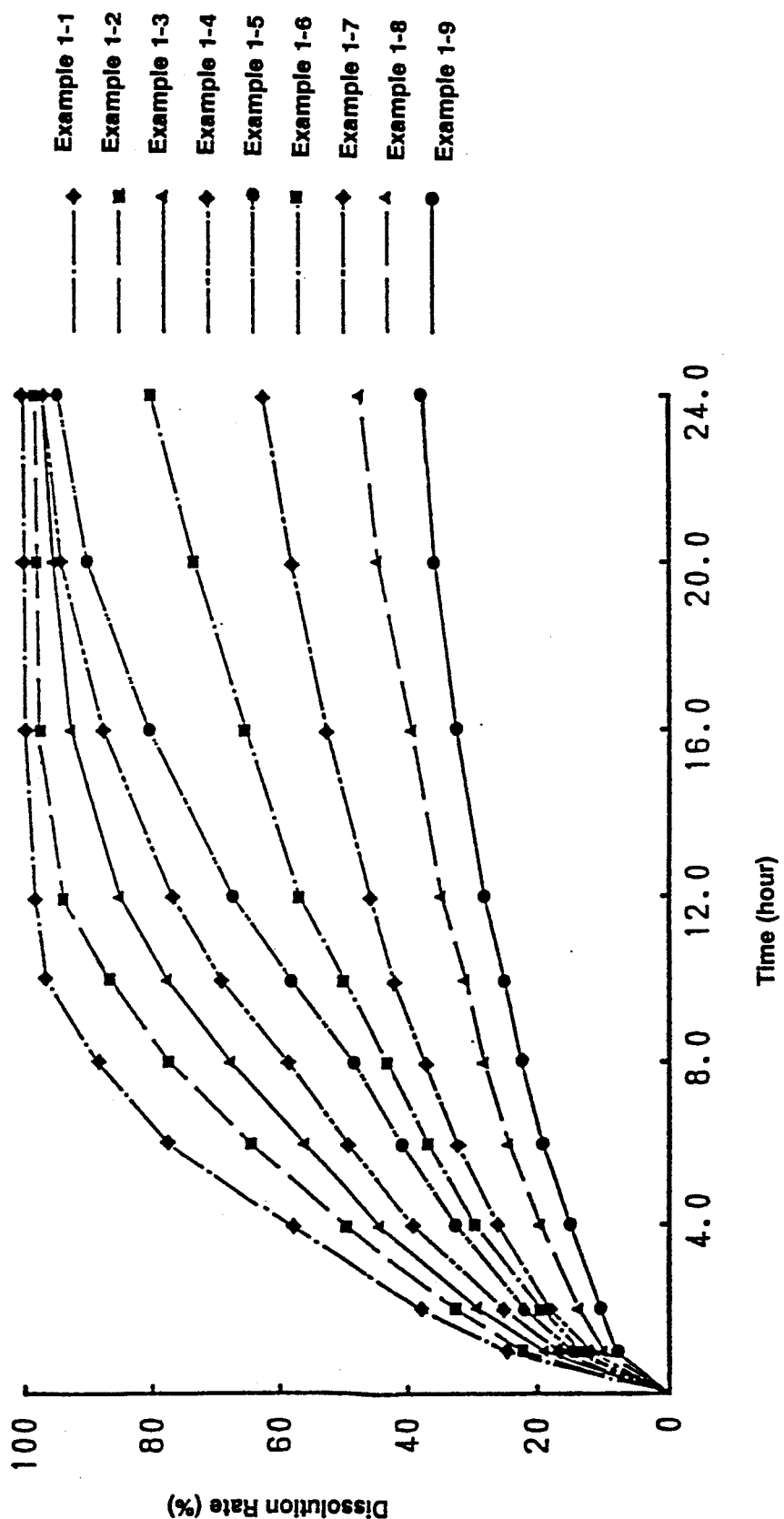
FIG. 1 is a graph showing the results of the dissolution test in Test Example 1 using the tablets of the present invention containing sustained-release powder (A) and sustained-release powder (B) at different ratios.

Oil components which can be used in sustained-release powder (A) include oils and fats, waxes, hydrocarbons, higher fatty acids, higher alcohols, esters, metal salts of higher fatty acids, and the like. Specific examples of oils and fats include plant oils, e.g. cacao butter, palm oil, Japan wax (wood wax), coconut oil, etc.; animal oils, e.g. beef tallow, lard, horse fat, mutton tallow, etc.; hydrogenated oils of animal origin, e.g. hydrogenated fish oil, hydrogenated whale oil, hydrogenated beef tallow, etc.; hydrogenated oils of plant origin, e.g. hydrogenated rape seed oil, hydrogenated castor oil, hydrogenated coconut oil, hydrogenated soybean oil, etc.; and the like. Of these hydrogenated oils are preferred as an oil component of the present invention. Specific examples of waxes include plant waxes, e.g. carnauba wax, candelilla wax, bayberry wax, auricurry wax, espalt wax, etc.; animal waxes, e.g. bees wax, breached bees wax, insect wax, spermaceti, shellac, lanolin, etc.; and the like. Of these preferred are carnauba wax, bees wax and breached bees wax. Paraffin, petrolatum, microcrystalline wax, and the like, are given as specific examples of hydrocarbons, with preferable hydrocarbons being paraffin and microcrystalline wax. Given as examples of higher fatty acids are caprilic acid, undecanoic acid, lauric acid, tridecanic acid, myristic acid, pentadecanoic acid, palmitic acid, malgaric acid, stearic acid, nonadecanic acid, arachic acid, heneicosanic acid, behenic acid, tricosanic acid, lignoceric acid, pentacosanic acid, cerotic acid, heptacosanic acid, montanic acid, nonacosanic acid, melissic acid, hentriacontanic acid, dotriacontanic acid, and the like. Of these, preferable are myristic acid, palmitic acid, stearic acid, and behenic acid. Specific examples of higher alcohols are lauryl alcohol, tridecyl alcohol, myristyl alcohol, pentadecyl alcohol, cetyl alcohol, heptadecyl alcohol, stearyl alcohol, nonadecyl alcohol, arachyl alcohol, behenyl alcohol, carnaubic alcohol, corianyl alcohol, ceryl alcohol, and myricyl alcohol. Particularly preferable alcohols are cetyl alcohol, stearyl alcohol, and the like. Specific examples of esters are fatty acid esters, e.g. myristyl palmitate, stearyl stearate, myristyl myristate, behenyl behenate, ceryl lignocerate, lacceryl cerotate, lacceryl laccerate, etc.; glycerine fatty acid esters, e.g. lauric monoglyceride, myristic monoglyceride, stearic monoglyceride, behenic monoglyceride, oleic monoglyceride, oleic stearic diglyceride, lauric diglyceride, myristic diglyceride, stearic diglyceride, lauric triglyceride, myristic triglyceride, stearic triglyceride, acetylstearic glyceride, hydoxystearic triglyceride, etc.; and the like. Glycerine fatty acid esters are more preferable. Specific examples of metal salts of higher fatty acid are calcium stearate, magnesium stearate, aluminum stearate, zinc stearate, zinc palmitate, zinc myristate, magnesium myristate, and the like, with preferable higher fatty acid salts being calcium stearate and magnesium stearate. As specific examples of water insoluble polymers, ethylcellulose, aminoalkyl methacrylate copolymer, cellulose acetate, polyvinyl acetate, polyvinyl chloride, and the like are given. Of these, ethylcellulose and aminoalkyl methacrylate copolymer are preferable.

These oil components and water insoluble polymers can be used either singly or in combination of two or more.

There are no specific restrictions as to the pharmaceutically active components used in the present invention. Typical examples of such components are drugs for the central nervous system, e.g. hypnotics, sedatives, antiepileptics, antipyretic analgesics, antiinflammatory drugs, stimulants, analeptic drugs, etc.; drugs for the peripheral nervous system, e.g. skeletal muscle relaxants, autonomic blocking agents, autonomic nerve blockers, plant preparations, etc.; drugs for sense-organs, e.g. drugs for eye- or ear-diseases, etc.; drugs for circulatory organs, e.g. cardiotonics, antiarrhythmic agents, diuretics, hypotensive agents, capillary stabilizers, vasoconstricors, vasodilators, antiarteriosclerosis agents, etc.; drugs for respiratory organs, e.g. respiratory stimulant, antitussive drugs, expectorants, etc.; drugs for digestive organs, e.g. peptic ulcer drugs, stomachics, digestants, antacids, cathartics, cholagogues, drugs for controlling intestinal functions, etc.; hormones and antihormones; drugs for urogenital organs and anus, e.g. urinary antiseptics, oxytocics, urogenital drugs, drugs for anus diseases, etc.; metabolic drugs, e.g. vitamins, aphrodisiacs, drugs for blood and body fluid, drugs for hepatic diseases, antidotes, drugs for habitual poisoning, drugs for treatment of gout, enzyme preparations, hypoglycemic drugs, etc.; tissue cell functional drugs, e.g. cell activation drugs, antimalignant neoplastic agents, etc.; chemical treatment drugs, e.g. antibiotics, sulfur agents, antituberculosis, etc.; drugs against pathogenic microorganisms, e.g. antiprotozoan drugs, anthelmintics, etc,; narcotics, e.g. alkaloid-type narcotics, non-alkaloid-type narcotics, etc.; and the like.

In order to ensure the effect of the present invention, it is desirable that the proportion of the oil components and/or water insoluble polymers for pharmaceutically active components in the sustained-release powder (A) be 5% by weight or more, and especially 7.5% by weight or more.

If necessary, suitable excipients, binders, and the like may be added to the sustained-release powder (A) in addition to the above essential components.

The method for the preparation of the sustained-release powder (A) is not specifically limited. They can easily be prepared, for instance, by a process comprising gradually adding molten oil components to pharmaceutically active components to which excipients or the like are optionally added, and granulating the mixture; a process comprising dispersing pharmaceutically active components to which excipients or the like are optionally added in molten oil components, and cooling and pulverizing the mixture; a process comprising the addition of oil components and/or water insoluble polymers and pharmaceutically active components to which excipients or the like are optionally added, followed by dry granulation; or a process comprising the addition of oil components and/or water insoluble polymers, and pharmaceutically active components to which excipients, binders, or the like are optionally added, followed by wet granulation. The granules thus obtained may be pulverized or classified.

The term "powder" in the present invention includes both powder and processed powders such as granule. The term "sustained-release powder" in the present invention is defined as the "powder" which can be made into tablets by press-molding, thereby delaying release of pharmaceutically active components. It does not matter whether or not the powder retards release of pharmaceutically active components before press-molding.

Water soluble polymers which are used in sustained-release powder (B) of the present invention may be any polymers which are soluble in water and can retard the release of pharmaceutically active components when made into tablets by press-molding. Preferred water soluble polymers are those which can form hydrocolloid when molded into tablets, thereby retarding release of pharmaceutically active components. They include naturally occurring or synthetic, anionic or nonionic, hydrophilic rubbers, cellulose derivatives, proteins, and the like. Specific examples are acacia, tragacanth, locust been gum, guarh-gum, karaya gum, pectin, arginic acid, propylene glycol arginate, hydroxypropyl methylcellulose, methylcellulose, hydroxypropyl cellulose, hydroxyethyl cellulose, carboxymethylcellulose sodium, polyvinylpyrrolidone, carboxyvinyl polymer, sodium polyacrylate, alpha starch, sodium carboxymethyl starch, dexstrin, agar, gelatin, casein, sodium casein, pullulan, polyvinyl alcohol, and the like. Of these, preferable are hydroxypropyl methylcellulose, methylcellulose, hydroxypropyl cellulose, and polyvinylpyrrolidone. These water soluble polymers can be used either singly or in combination of two or more. Furthermore, depending on the solubility, the amount, etc. of pharmaceutically active components, they may be used together with conventionally known excipients, binders, and the like, such as lactose, sucrose, glucose, polyethylene glycol, polyoxyethylene polyoxypopylene glycol, and the like.

There are no specific restrictions as to the pharmaceutically active components to be incorporated in the sustained-release powder (B). The same or different pharmaceutically active components as used in sustained-release powder (A) can be used.

It is desirable in order to ensure the effect of the present invention to incorporate 2% by weight or more of water soluble polymers for the amount of the pharmaceutically active components in the sustained-release powder (B). Besides these essential components, excipients, binders, etc. may be added to the sustained-release powder (B), as required.

There are no specific restrictions as to the methods of manufacture of the sustained-release powder (B). It can easily be prepared, for instance, by the dry granulation of a mixture containing water soluble polymers, pharmaceutically active components, and optionally, excipients and the like; or by the wet granulation of a mixture containing water soluble polymers, pharmaceutically active components, and optionally, excipients, binders, and the like. The granules thus obtained may be pulverized or classified.

The sustained-release tablets of the present invention can be prepared according to a conventional method by press-molding a mixture of the above-mentioned sustained-release powders (A) and (B), and, optionally, additives necessary for the press-molding. A preferable ratio by weight of the sustained-release powders (A) and (B) is 1:9–9:1, with especially preferable range being 2:8–7:3. If desired, excipients, binders, lubricants, and the like can be added to the mixture to be molded.

The sustained-release tablets thus prepared can be used as are, or further made into cored tablets or multi-layer tablets by combining components with sustained-release powders (A) and (B) with different release rates in separate layers. Furthermore, they can be made into film-coated tablets or sugar-coated tablets.

When theophylline is used as a pharmaceutically active component, one preferable embodiment of the tablets of the present invention is those prepared by tabletting a mixture of sustained-release powder (A) comprising stearic acid, hydrogenated oil, and glycerine fatty acid ester in an amount of 5% by weight or more for theophylline and sustained-release powder (B) comprising hydroxypropyl methylcellulose in an amount of 2% by weight or more for theophylline, at a ration (A):(B) of 1:9–9:1, and, optionally, a lubricant, e.g. magnesium stearate.

In the sustained-release tablets of the present invention, an ideal release rate for individual pharmaceutically active component can be ensured by controlling its release rate by changing the ratio of the sustained-release powders (A) and (B). Excellent reproducibility in the release rate is also ensured by the tablets of the present invention. Furthermore, when the amount of the pharmaceutically active component in the sustained-release powders (A) and (B) are the same, it is possible to control the release rate by changing the ratio of powders (A) and (B) without changing the weight or the shape of the tablets.

Other features of the invention will become apparent in the course of the following description of the exemplary embodiments which are given for illustration of the invention and are not intended to be limiting thereof.

EXAMPLES

Example 1

A mixture of 140 gm of stearic acid, 130 gm of hydrogenated castor oil, and 130 gm of glycerine fatty acid ester was heated to melt, and was added to 600 gm of theophylline. The mixture was kneaded, cooled and pulverized to obtain a sustained-release powder (A).

600 gm of theophylline, 50 gm of hydroxypropyl methylcellulose, and 350 gm of lactose were mixed, followed by the addition of 400 gm of purified water. The mixture was kneaded, dried and pulverized to obtain a sustained-release powder (B).

The sustained-release powders (A) and (B) were mixed together with magnesium stearate at the proportions listed in Table 1. The mixtures were made into tablets, each weighing 337 mg, by a die punch with a diameter of 9 mm to obtain sustained-release tablets of the present invention. Each tablet contained 200 mg of theophylline.

TABLE 1

| Example No. | Sustained-release Powder (A) | Sustained-release Powder (B) | Magnesium Stearate | Total |
|---|---|---|---|---|
| 1-1 | 10 gm | 90 gm | 1 gm | 101 gm |
| 1-2 | 20 gm | 80 gm | 1 gm | 101 gm |
| 1-3 | 30 gm | 70 gm | 1 gm | 101 gm |
| 1-4 | 40 gm | 60 gm | 1 gm | 101 gm |
| 1-5 | 50 gm | 50 gm | 1 gm | 101 gm |
| 1-6 | 60 gm | 40 gm | 1 gm | 101 gm |
| 1-7 | 70 gm | 30 gm | 1 gm | 101 gm |
| 1-8 | 80 gm | 20 gm | 1 gm | 101 gm |
| 1-9 | 90 gm | 10 gm | 1 gm | 101 gm |

Test Example 1

The dissolution of active component from the sustained-release tablets prepared in Example 1 were measured by the rotating paddle method (Japan Pharmacopeia, 11th Edition, Dissolution Test) at a rotation of 50 r.p.m. and using a buffer test solution of pH 6.8 (Japan Pharmacopeia, 11th Edition, Disintegration Test Solution No. 2). The results are given in FIG. 1, which shows that the sustained-release tablets of the present invention release theophylline over a long period of time, and further that the release rate can successively be controlled by changing the proportion of the sustained-release powders (A) and (B).

Test Example 2

Figure 2:
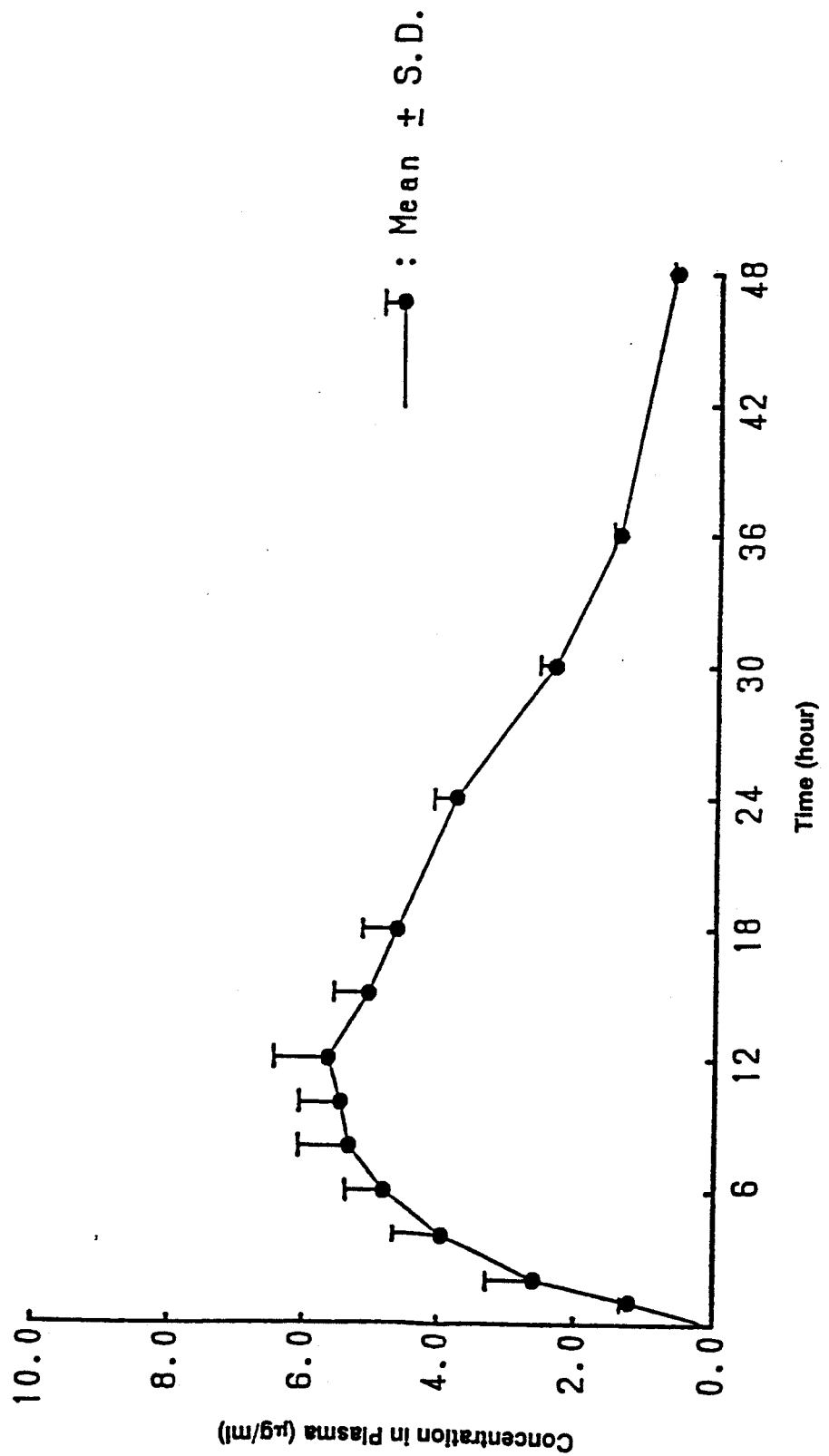
FIG. 2 is a graph showing the results of Test Example 2, in which the changes in the theophylline concentration in plasma of human subjects to which tablets of the present invention was administered are shown.

Two tablets prepared in Examples 1-5 were administered to 3 healthy adult men to measure the concentration of theophylline in blood. The results are presented in FIG. 2, which showed little variations among the subjects in the blood concentration, demonstrating good sustained release of the component into blood.

Comparative Example 1

A mixture of 140 gm of stearic acid, 130 gm of hydrogenated castor oil, and 130 gm of glycerine fatty acid ester was heated to melt, and was added to of 600 gm of theophylline. The mixture was kneaded, cooled and pulverized to obtain a sustained-release powder (A). gm of theophylline, 200 gm of microcrystalline cellulose, 100 gm of croscarmellose sodium type-A, and 100 gm of lactose were mixed, followed by the addition of 400 gm of purified water. The mixture was kneaded, dried and pulverized to obtain a comparative fast-release powder (C). The powders (A) and (C) were mixed together with magnesium stearate at the proportions listed in Table 2. The mixtures were made into tablets, each weighing 337 mg, by a die punch with a diameter of 9 mm to obtain comparative tablets. Each tablet contained 200 mg of theophylline.

TABLE 2

| Comparative Example No. | Sustained-release Powder (A) | Fast-release Powder (C) | Magnesium Stearate | Total |
| --- | --- | --- | --- | --- |
| 1-1 | 10 gm | 90 gm | 1 gm | 101 gm |
| 1-2 | 20 gm | 80 gm | 1 gm | 101 gm |
| 1-3 | 30 gm | 70 gm | 1 gm | 101 gm |
| 1-4 | 40 gm | 60 gm | 1 gm | 101 gm |
| 1-5 | 50 gm | 50 gm | 1 gm | 101 gm |
| 1-6 | 60 gm | 40 gm | 1 gm | 101 gm |
| 1-7 | 70 gm | 30 gm | 1 gm | 101 gm |
| 1-8 | 80 gm | 20 gm | 1 gm | 101 gm |
| 1-9 | 90 gm | 10 gm | 1 gm | 101 gm |

Comparative Test Example 1

Figure 3:
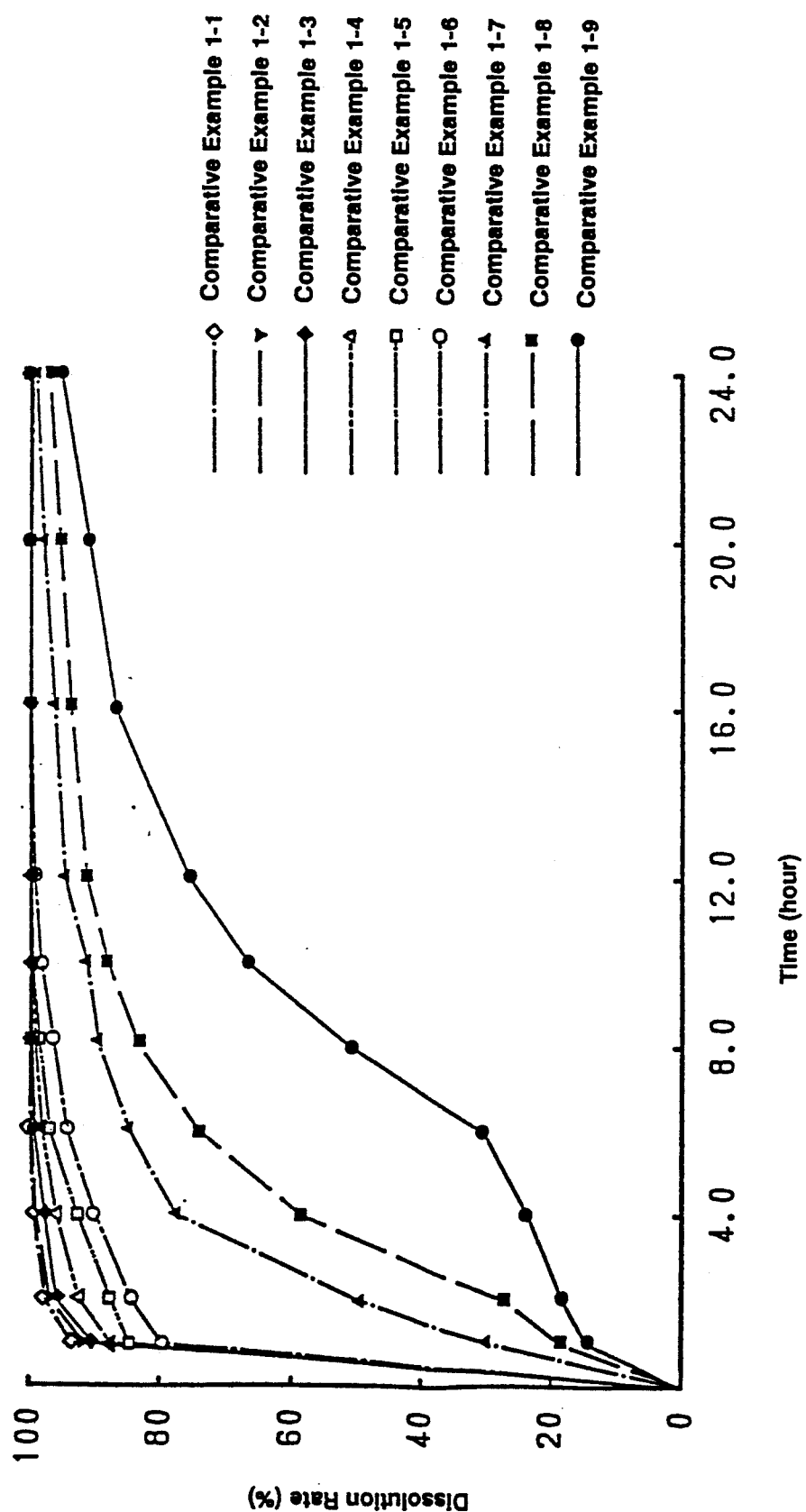
FIG. 3 is a graph showing the results of the dissolution test in Comparative Test Example 1 using the tablets prepared in Comparative Example 1.

The dissolution of active component from the tablets prepared in Comparative Example 1 were measured by the rotating paddle method (Japan Pharmacopeia, 11th Edition, Dissolution Test) at a rotation of 50 r.p.m. and using a buffer test solution of pH 6.8 (Japan Pharmacopeia, 11th Edition, Disintegration Test Solution No.2). The results are given in FIG. 3, which shows that, while it is possible to successively control the release rate of theophylline from the tablets of the present invention by changing the proportion of the sustained-release powders (A) and (B), it is difficult to control the release rate successively from the tablets in which comparative fast-releasing powder (C) was used instead of the sustained-release powder (B).

Comparative Example 2

600 gm of theophylline, 50 gm of hydroxypropyl methylcellulose, and 350 gm of lactose were mixed, followed by the addition of 400 gm of purified water. The mixture was kneaded, dried and pulverized to obtain a sustained-release powder (B) in the same manner as in Example 1.

600 gm of theophylline, 200 gm of microcrystalline cellulose, 100 gm of croscarmellose sodium type-A, and 100 gm of lactose were mixed, followed by the addition of 400 gm of purified water. The mixture was kneaded, dried and pulverized to obtain a comparative fast-release powder (C) in the same manner as in Example 1.

The powders (B) and (C) were mixed together with magnesium stearate at the proportions listed in Table 3. The mixtures were made into tablets, each weighing 337 mg, by a die punch with a diameter of 9 mm to obtain comparative tablets. Each tablet contained 200 mg of theophylline.

TABLE 3

| Comparative Example No. | Sustained-release Powder (B) | Fast-release Powder (C) | Magnesium Stearate | Total |
| --- | --- | --- | --- | --- |
| 2-1 | 10 gm | 90 gm | 1 gm | 101 gm |
| 2-2 | 20 gm | 80 gm | 1 gm | 101 gm |
| 2-3 | 30 gm | 70 gm | 1 gm | 101 gm |
| 2-4 | 40 gm | 60 gm | 1 gm | 101 gm |
| 2-5 | 50 gm | 50 gm | 1 gm | 101 gm |
| 2-6 | 60 gm | 40 gm | 1 gm | 101 gm |
| 2-7 | 70 gm | 30 gm | 1 gm | 101 gm |

TABLE 3-continued

| Comparative Example No. | Sustained-release Powder (B) | Fast-release Powder (C) | Magnesium Stearate | Total |
| --- | --- | --- | --- | --- |
| 2-8 | 80 gm | 20 gm | 1 gm | 101 gm |
| 2-9 | 90 gm | 10 gm | 1 gm | 101 gm |

Comparative Test Example 2

Figure 4:
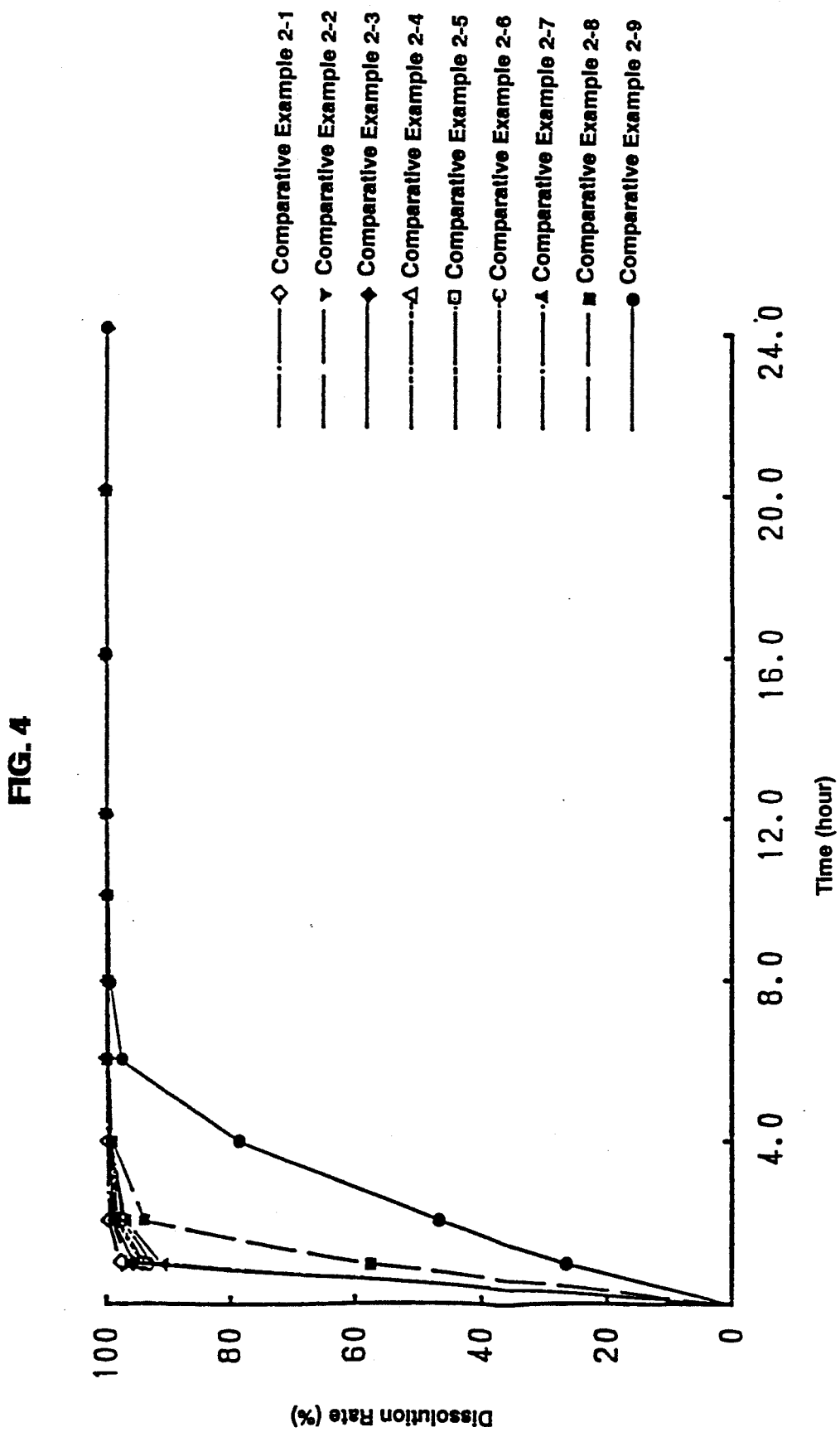
FIG. 4 is a graph showing the results of the dissolution test in Comparative Test Example 2 using the tablets prepared in Comparative Example 2.

The dissolution of active component from the tablets prepared in Comparative Example 2 were measured by the rotating paddle method (Japan Pharmacopeia, 11th Edition, Dissolution Test) at a rotation of 50 r.p.m. and using a buffer test solution of pH 6.8 (Japan Pharmacopeia, 11th Edition, Disintegration Test Solution No. 2). The results are given in FIG. 4, which shows that, while it is possible to successively control the release rate of theophylline from the tablets of the present invention by changing the proportion of the sustained-release powders (A) and (B), it is difficult to control the release rate from the tablets in which comparative fast-releasing powder (C) was used instead of the sustained-release powder (A).

Example 2

Sustained-release powder (A) was prepared by adding 500 gm of diclofenac sodium to 500 gm of stearyl alcohol which had been heated to melt, followed by cooling and pulverization.

Sustained-release powder (B) was prepared by mixing 500 gm of diclofenac sodium, 250 gm of hydroxypropyl cellulose, and 250 gm of lactose, and adding 200 gm of ethyl alcohol to the mixture, followed by kneading, drying, and pulverization.

The sustained-release powders (A) and (B) were mixed together with magnesium stearate at the proportions listed in Table 4. The mixtures were made into tablets, each weighing 202 mg, by a die punch with a diameter of 8 mm to obtain sustained-release tablets of the present invention. Each tablet contained 100 mg of diclofenac sodium.

TABLE 4

| Example No. | Sustained-release Powder (A) | Sustained-release Powder (B) | Magnesium Stearate | Total |
| --- | --- | --- | --- | --- |
| 2-1 | 25 gm | 75 gm | 1 gm | 101 gm |
| 2-2 | 50 gm | 50 gm | 1 gm | 101 gm |
| 2-3 | 75 gm | 25 gm | 1 gm | 101 gm |

Test Example 3

Figure 5:
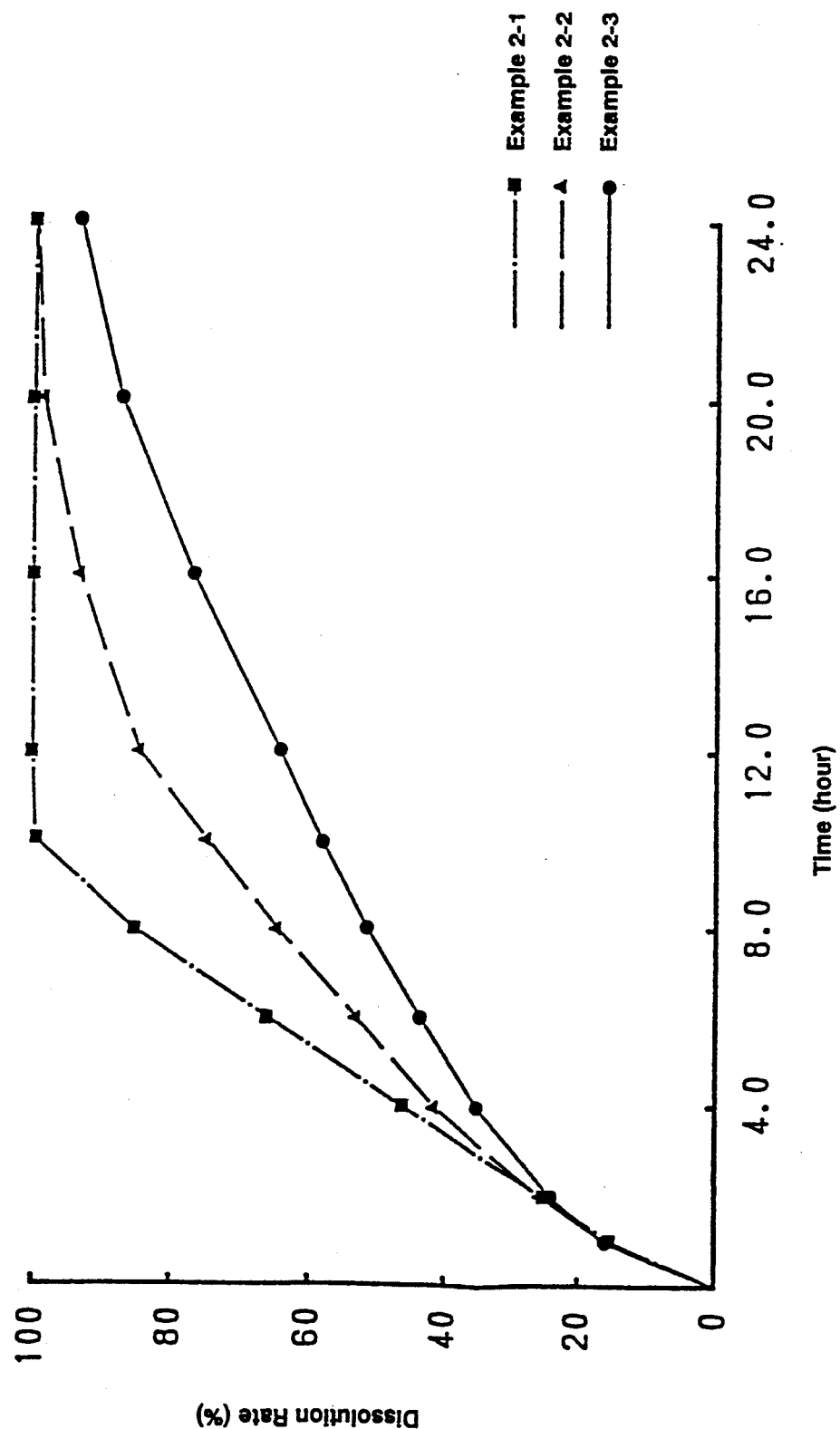
FIG. 5 is a graph showing the results of the dissolution test in Test Example 3 from the tablets of the present invention containing sustained-release powder (A) and sustained-release powder (B) at different ratios.

The dissolution of active component from the sustained-release tablets prepared in Example 2 were measured by the rotating paddle method (Japan Pharmacopeia, 11th Edition, Dissolution Test) at a rotation of 50 r.p.m. and using a buffer test solution of pH 6.8 (Japan Pharmacopeia, 11th Edition, Disintegration Test Solution No. 2). The results are given in FIG. 5, which shows that the sustained-release tablets of the present invention release diclofenac sodium over a long period of time, and further that the release rate can be controlled by changing the proportion of the sustained-release powders (A) and (B).

Example 3

Sustained-release powder (A) was prepared by adding 250 gm of bisbentiamine to a mixture of 250 gm of stearic acid, 250 gm of hydrogenated castor oil, and 250 gm of glycerine fatty acid ester, which had been heated to melt, followed by cooling and pulverization. Sustained-release powder (B) was prepared by mixing 250 gm of bisbentiamine, 250 gm of hydroxypropyl methylcellulose, and 500 gm of lactose, and adding 450 gm of purified water to the mixture, followed by kneading, drying, and pulverization.

The sustained-release powders (A) and (B) were mixed together with magnesium stearate at the proportions listed in Table 5. The mixtures were made into tablets, each weighing 101 mg, by a die punch with a diameter of 7 mm to obtain sustained-release tablets of the present invention. Each tablet contained 25 mg of bisbentiamine.

TABLE 5

| Example No. | Sustained-release Powder (A) | Sustained-release Powder (B) | Magnesium Stearate | Total |
|---|---|---|---|---|
| 3-1 | 25 gm | 75 gm | 1 gm | 101 gm |
| 3-2 | 50 gm | 50 gm | 1 gm | 101 gm |
| 3-3 | 75 gm | 25 gm | 1 gm | 101 gm |

Test Example 4

Figure 6:
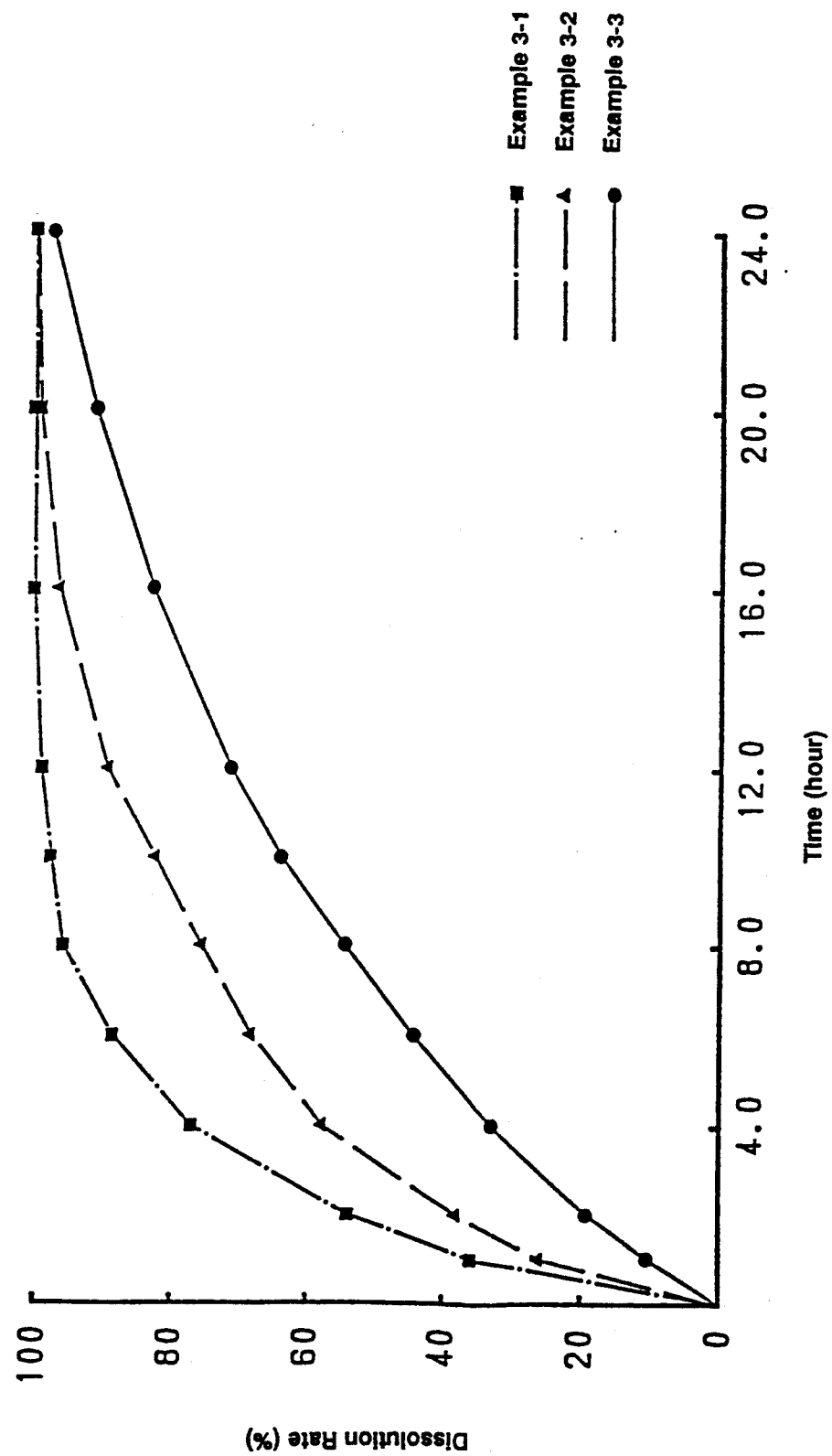
FIG. 6 is a graph showing the results of the dissolution test in Test Example 4 using the tablets of the present invention containing sustained-release powder (A) and sustained-release powder (B) at different ratios.

The dissolution of active component from the sustained-release tablets prepared in Example 3 were measured by the rotating paddle method (Japan Pharmacopeia, 11th Edition, Dissolution Test) at a rotation of 50 r.p.m. and using a buffer test solution of pH 1.2 (Japan Pharmacopeia, 11th Edition, Disintegration Test Solution No. 1). The results are given in FIG. 6, which shows that the sustained-release tablets of the present invention release bisbentiamine over a long period of time, and further that the release rate can be controlled by changing the proportion of the sustained-release powders (A) and (B).

Example 4

Sustained-release powder (A) was prepared by adding 500 gm of trapidil to a mixture of 100 gm of stearic acid, 300 gm of hydrogenated castor oil, and 100 gm of glycerine fatty acid ester, which had been heated to melt, followed by kneading, cooling and pulverization.

Sustained-release powder (B) was prepared by mixing 500 gm of trapidil, 100 gm of hydroxypropyl methylcellulose, and 400 gm of lactose, and adding 400 gm of purified water to the mixture, followed by kneading, drying, and pulverization.

The sustained-release powders (A) and (B) were mixed together with magnesium stearate at the proportions listed in Table 6. The mixtures were made into tablets, each weighing 606 mg, by a die punch with a diameter of 11 mm to obtain sustained-release tablets of the present invention. Each tablet contained 300 mg of trapidil.

TABLE 6

| Example No. | Sustained-release Powder (A) | Sustained-release Powder (B) | Magnesium Stearate | Total |
|---|---|---|---|---|
| 4-1 | 25 gm | 75 gm | 1 gm | 101 gm |
| 4-2 | 50 gm | 50 gm | 1 gm | 101 gm |
| 4-3 | 75 gm | 25 gm | 1 gm | 101 gm |

Test Example 5

Figure 7:
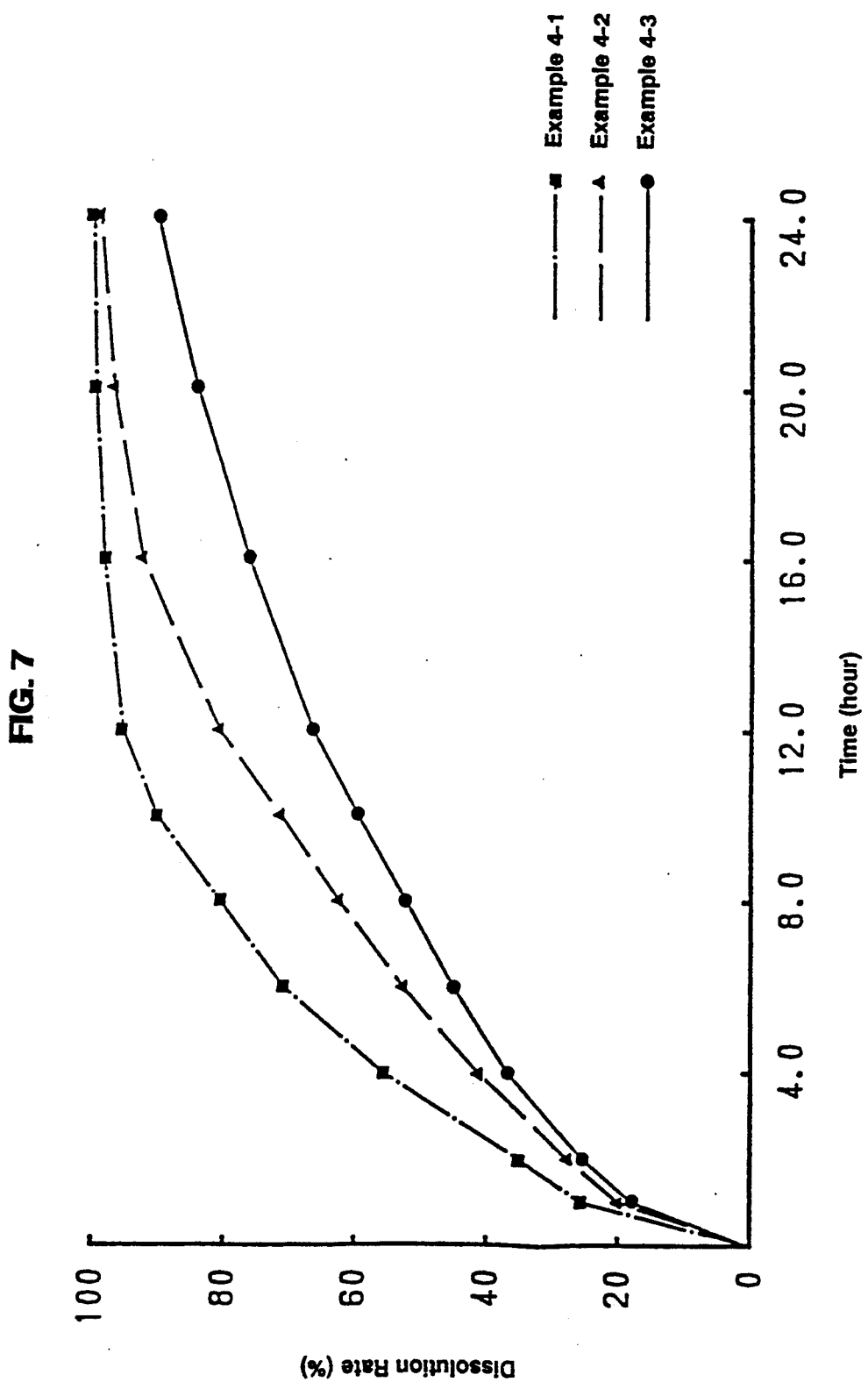
FIG. 7 is a graph showing the results of the dissolution test in Test Example 5 using the tablets of the present invention containing sustained-release powder (A) and sustained-release powder (B) at different ratios.

The dissolution of active component from the sustained-release tablets prepared in Example 4 were measured by the rotating paddle method (Japan Pharmacopeia, 11th Edition, Dissolution Test) at a rotation of 50 r.p.m. and using a buffer test solution of pH 6.8 (Japan Pharmacopeia, 11th Edition, Disintegration Test Solution No. 2). The results are given in FIG. 7, which shows that the sustained-release tablets of the present invention release trapidil over a long period of time, and further that the release rate can be controlled by changing the proportion of the sustained-release powders (A) and (B).

Example 5

600 gm of theophylline, 150 gm of hydrogenated vegetable oil, 50 gm of microcrystalline cellulose, 50 gm of hydroxypropyl methylcellulose, and 30 gm of lactose were mixed. 333.3 gm of aqueous dispersion of ethylcellulose (100 gm as solid portion) and 20 gm of glycerine fatty acid ester were added to the mixture, and the resulting mixture was kneaded, dried, and pulverized to obtain a sustained-release powder (A).

600 gm of theophylline, 150 gm of hydroxypropyl methylcellulose, 100 gm of microcrystalline cellulose, 100 gm of lactose, and 50 gm of hydroxypropyl methylcellulose acetate succinate were mixed. After the addition of a mixture of 50 gm of ethyl alcohol and 350 gm of purified water, the resulting mixture was kneaded, dried, and pulverized to obtain a sustained-release powder (B).

The sustained-release powders (A) and (B), each 333.5 gm, were mixed together with 7 gm of magnesium stearate. The mixtures were made into tablets, each weighing 337 mg, by a die punch with a diameter of 9 mm to obtain sustained-release tablets of the present invention. Each tablet contained 200 mg of theophylline.

Test Example 6

Figure 8:
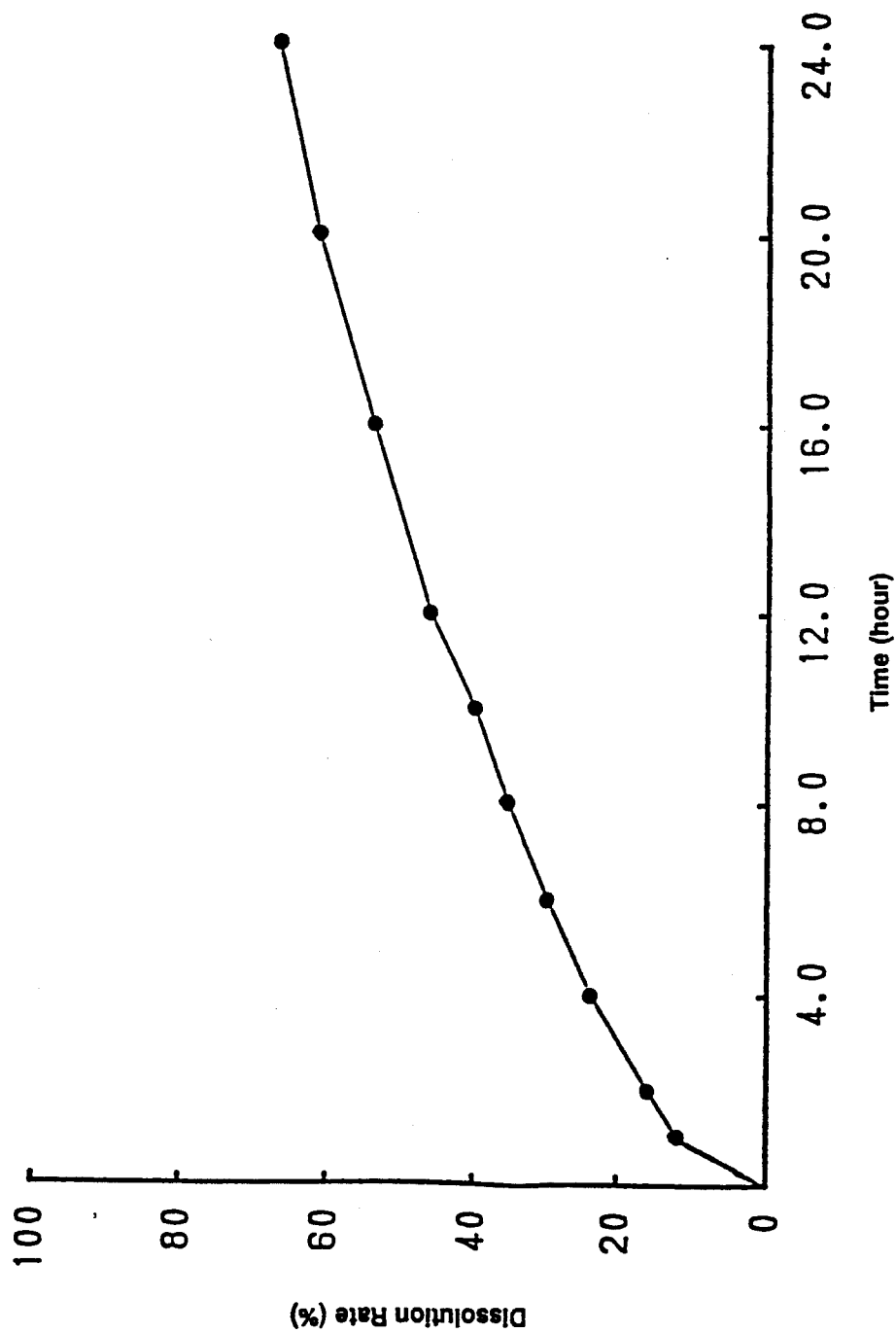
FIG. 8 is a graph showing the results of the dissolution test in Test Example 6 using the tablets of the present invention in which an oil component and a water insoluble polymer are used as release control agents in sustained-release powder (A).

The dissolution of active component from the sustained-release tablets prepared in Example 5 were measured by the rotating paddle method (Japan Pharmacopeia, 11th Edition, Dissolution Test) at a rotation of 50 r.p.m. and using a buffer test solution of pH 6.8 (Japan Pharmacopeia, 11th Edition, Disintegration Test Solution No. 2). The results are shown in FIG. 8, by which theophylline was confirmed to be released from the tablets of the present invention over a long period of time.

Example 6

(1) Sustained-release powders W-1 to W-3 containing oil components were prepared by heating mixtures of stearic acid, hydrogenated castor oil, and glycerine fatty acid ester, and adding the mixture to theophylline, followed by kneading, cooling, and pulverization. Formulas of W-1 to W-3 are shown in Table 7.

TABLE 7

| Components | W-1 | W-2 | W-3 (gm) |
|---|---|---|---|
| Theophylline | 400 | 400 | 400 |
| Stearic acid | 6.8 | 10.2 | 13.6 |
| Hydrogenated castor oil | 6.6 | 9.9 | 13.2 |
| Glycerine fatty acid ester | 6.6 | 9.9 | 13.2 |
| Total | 420 | 430 | 440 |
| Proportion wt. % of oil components for Theophylline | 5 | 7.5 | 10 |

(2) Sustained-release powders P-1 and P-2 containing a water soluble polymer were prepared by mixing hydroxypropyl methylcellulose and theophylline, and adding purified water to the mixture, followed by kneading, drying, and pulverization. Formulas of P-1 and P-2 are shown in Table 8.

TABLE 8

| Components | P-1 | P-2 (gm) |
|---|---|---|
| Theophylline | 400 | 400 |
| Hydroxypropyl methyl cellulose | 8 | 20 |
| Total | 408 | 420 |
| Proportion wt. % of a water soluble polymer for Theophylline | 2 | 5 |

(3) Tablets T-1 to T-12 of the present invention were prepared from powders W-1 to W-3 and powders P-1 and P-2 in various proportions together with magnesium stearate (2 mg/tablet) by a die punch with a diameter of 8 mm. Formulas of the tablets are listed in Table 9. Each tablet contained 200 mg of theophylline.

TABLE 9

| Tablet | Powders W-Series (mg) | Powders P-Series (mg) | Magnesium Stearate (mg) | Total (mg) |
|---|---|---|---|---|
| T-1 | W-1 157.5 | P-1 51 | 2 | 210.5 |
| T-2 | W-1 105 | P-1 102 | 2 | 209 |
| T-3 | W-1 52.5 | P-1 153 | 2 | 207.5 |
| T-4 | W-2 161.25 | P-1 51 | 2 | 212.25 |
| T-5 | W-2 107.5 | P-1 102 | 2 | 211.5 |
| T-6 | W-2 53.75 | P-1 153 | 2 | 208.75 |
| T-7 | W-3 165 | P-1 51 | 2 | 218 |
| T-8 | W-3 110 | P-1 102 | 2 | 214 |
| T-9 | W-3 55 | P-1 153 | 2 | 210 |
| T-10 | W-1 157.5 | P-2 52.5 | 2 | 212 |
| T-11 | W-1 105 | P-2 105 | 2 | 212 |
| T-12 | W-1 52.5 | P-2 157.5 | 2 | 212 |

Test Example 7

The dissolution of active component from the sustained-release tablets prepared in Example 6 were measured by the rotating paddle method (Japan Pharmacopeia, 11th Edition, Dissolution Test) at a rotation of 50 r.p.m. and using a buffer test solution of pH 6.8 (Japan Pharmacopeia, 11th Edition, Disintegration Test Solution No. 2). The results are shown in Table 10, which demonstrates that the release rate can be controlled by changing the proportion of the sustained-release powder containing oil components and the sustained-release powder containing water soluble polymers.

TABLE 10

| Tablet | Rate of Dissolution (%) | | |
|---|---|---|---|
| | After 2 hours | After 4 hours | After 6 hours |
| T-1 | 45.4 | 87.8 | 95.3 |
| T-2 | 48.0 | 89.2 | 97.5 |
| T-3 | 51.7 | 89.2 | 97.8 |

TABLE 10-continued

| Tablet | Rate of Dissolution (%) | | |
|---|---|---|---|
| | After 2 hours | After 4 hours | After 6 hours |
| T-4 | 40.5 | 62.1 | 76.3 |
| T-5 | 42.1 | 65.4 | 80.5 |
| T-6 | 46.9 | 70.6 | 86.7 |
| T-7 | 32.4 | 52.3 | 67.4 |
| T-8 | 37.4 | 60.3 | 78.9 |
| T-9 | 43.7 | 72.3 | 88.2 |
| T-10 | 47.2 | 78.4 | 95.3 |
| T-11 | 42.3 | 74.6 | 93.2 |
| T-12 | 40.3 | 72.8 | 92.1 |

Example 7

600 gm of theophylline, 200 gm of ethylcellulose, 50 gm of microcrystalline cellulose, and 50 gm of lactose were mixed. 333.3 gm of aqueous dispersion of ethylcellulose (100 gm as solid portion) was added to the mixture, and the resulting mixture was kneaded, dried, and pulverized to obtain a sustained-release powder (A).

600 gm of theophylline, 200 gm of hydroxypropyl methylcellulose, 100 gm of microcrystalline cellulose, and 100 gm of lactose were mixed. After the addition of 300 gm of purified water, the mixture was kneaded, dried, and pulverized to obtain a sustained-release powder (B).

167 gm of the sustained-release powder (A) and 500 gm of the sustained-release powder (B) were mixed together with 7 gm of magnesium stearate. The mixtures were made into tablets, each weighing 337 mg, by a die punch with a diameter of 9 mm to obtain sustained-release tablets of the present invention. Each tablet contained 200 mg of theophylline.

Test Example 8

Figure 9:
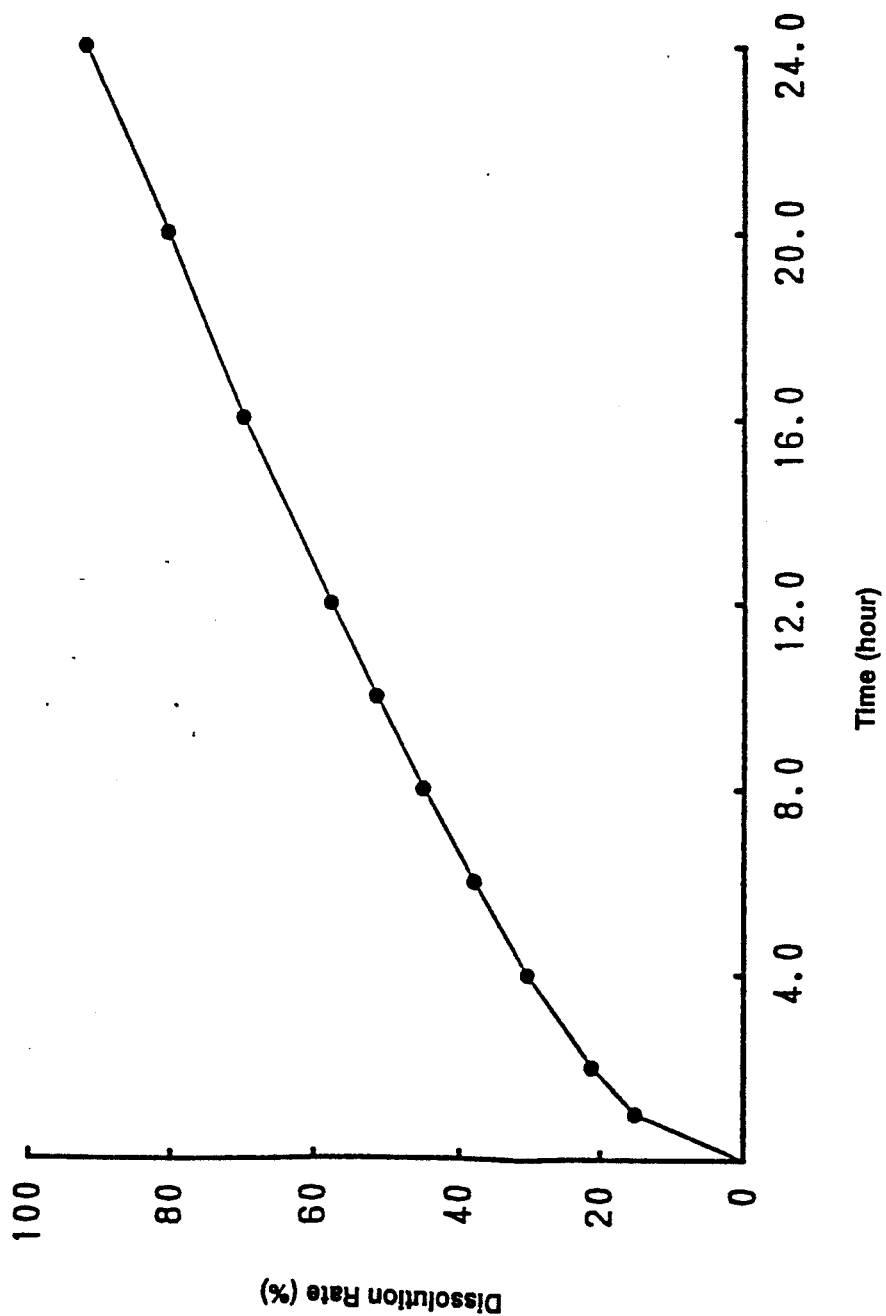
FIG. 9 is a graph showing the results of a dissolution test using the tablets prepared in Example 7 of the present invention in which a water insoluble polymer is used as a release control agent in sustained-release powder (A).

The dissolution of active component from the sustained-release tablets prepared in Example 7 were measured by the rotating paddle method (Japan Pharmacopeia, 11th Edition, Dissolution Test) at a rotation of 50 r.p.m. and using a buffer test solution of pH 6.8 (Japan Pharmacopeia, 11th Edition, Disintegration Test Solution No. 2). The results are shown in FIG. 9, by which theophylline was confirmed to be released from the tablets of the present invention over a long period of time.

Obviously, numerous modifications and variations of the present invention are possible in light of the above teachings. It is therefore to be understood that within the scope of the appended claims, the invention may be practiced otherwise than as specifically described herein.

What is claimed is:

1. A sustained-release tablet, which comprises:
(A) a sustained-release powder, comprising an effective amount of at least one member selected from the group consisting of oil components and water-insoluble polymers, and a pharmaceutically active component, and
(B) a sustained-release powder, comprising an effective amount of a water-soluble polymer and a pharmaceutically active component,
wherein said water-insoluble polymer is selected from the group consisting of ethylcellulose, aminoalkyl methacrylate copolymer, polyvinyl acetate, and polyvinyl chloride; and wherein the sustained-release powders (A) and (B) are used in a weight ratio of about 1:9-9:1, respectively.

2. The sustained-release tablet according to claim 1, wherein said water-soluble polymer is used in the amount of 2% by weight or more based on the amount of pharmaceutically active components.

3. The sustained-release tablet according to claim 1, wherein said water-soluble polymer of powder (B) is one or more compounds selected from the group consisting of naturally occurring or synthetic, anionic or nonionic, hydrophilic rubbers, cellulose derivatives, and proteins.

4. The sustained-release tablet according to claim 1, wherein the amount of oil components or water insoluble polymers, or both for the pharmaceutically active component contained in powder (A) is 5% by weight or more.

5. The sustained-release tablet according to claim 1, wherein the amount of water-soluble polymer for the pharmaceutically active component contained in powder (B) is 2% by weight or more.

6. The sustained-release tablet according to claim 1, wherein said water-insoluble polymer is ethylcellulose or aminoalkyl methacrylate polymer.

7. The sustained-release tablet according to claim 1, wherein the powders (A) and (B) are used in the range of about 2:8-7:3, respectively.

8. The sustained-release tablet according to claim 1, wherein said oil components are present in the amount of 5% by weight or more.

9. The sustained-release tablet according to claim 8, wherein the oil components are present in the amount of 7.5% by weight or more.

10. The sustained-release tablet according to claim 3, wherein said water-soluble polymer of powder (B) is selected from the group consisting of hydroxypropyl methylcellulose, methylcellulose, hydroxypropyl cellulose and polyvinylpyrrolidone.

11. The sustained-release tablet according to claim 1, wherein said oil component in powder (A) is one or more compounds selected from the group consisting of oils and fats, waxes, hydrocarbons, higher fatty acids, higher alcohols, esters, and metal salts of higher fatty acids.

12. The sustained-release tablet according to claim 11, wherein said oil is a hydrogenated oil.

13. The sustained-release tablet according to claim 11, wherein said wax is carnauba wax, bees wax or breached bees wax.

14. The sustained-release tablet according to claim 11, wherein said hydrocarbon is paraffin or microcrystalline wax.

15. The sustained-release tablet according to claim 11, wherein said higher fatty acid is myristic acid, palmitic acid, stearic acid or behenic acid.

16. The sustained-release tablet according to claim 11, wherein said higher alcohol is cetyl alcohol or stearyl alcohol.

17. The sustained-release tablet according to claim 11, wherein said esters are glycerine fatty acid esters.

18. The sustained-release tablet according to claim 11, wherein said metal salts of higher fatty acids are calcium stearate or magnesium stearate.

* * * * *